United States Patent [19]

Goodner et al.

[11] 4,046,820

[45] Sept. 6, 1977

[54] STABILIZATION OF 1,1,1-TRICHLOROETHANE

[75] Inventors: Willis Ray Goodner, Chandler; James Nelson Smith, Tempe; John Horvath, Chandler, all of Ariz.

[73] Assignee: Motorola, Inc., Schaumburg, Ill.

[21] Appl. No.: 693,588

[22] Filed: June 7, 1976

[51] Int. Cl.² .............................................. C07C 17/40
[52] U.S. Cl. .............................. 260/652.5 R; 252/171; 252/364; 134/40
[58] Field of Search ................. 260/652.5 R; 252/171, 252/364

[56] References Cited
U.S. PATENT DOCUMENTS 3,326,988  6/1967  Stack .......................... 260/653.5 R

*Primary Examiner*—C. Davis
*Attorney, Agent, or Firm*—John A. Fisher

[57] ABSTRACT

Improved stabilization of 1,1,1-trichloroethane is obtained by employing a free radical scavenger as a stabilizer which will trap trichloromethyl radicals, making them unavailable for formation of acidic species in the trichloroethane. Examples of such free radical scavengers include trichloroethylene, tetrachloroethylene, or fluorene. Compositions in accordance with the invention consist essentially of the 1,1,1-trichloroethane and from about 0.1 volume percent to about 5 volume percent of the free radical scavenger. In the fabrication of semiconductor devices in which the so stabilized trichloroethane is employed as a degreasing solvent, the acidity of the trichloroethane composition may be monitored, and additional free radical scavenger added to the solution to maintain the acidity within acceptable limits, thus allowing the trichloroethane to be used indefinitely.

4 Claims, No Drawings

STABILIZATION OF 1,1,1-TRICHLOROETHANE

BACKGROUND OF THE INVENTION

1. Field of the Invention.

This invention relates to an improved stabilizer and method for stabilizing 1,1,1-trichloroethane. More particularly, it relates to the use of free radical scavengers as stabilizing agents for trichloroethane. Most especially, it relates to a process for making semiconductor and related devices in which trichloroethane stabilized with a free radical scavenger is employed as a degreasing solvent in the process.

2. Description of the Prior Art.

Because of their highly desirable solvent properties, chlorinated hydrocarbon solvents are widely used in industrial processes. The one major drawback that these solvents have as a group is their instability. The decomposition of these solvents produces acids, is caused by the presence of light or air, and is catalyzed by such metals as iron, aluminum, magnesium, and their alloys. The presence of acid decomposition products further serves to increase the breakdown of these solvents. As pointed out in, for example, U.S. Pat. No. 3,787,509, the decomposition problem is particularly severe in the case of 1,1,1-trichloroethane. As pointed out in, for example, U.S. Pat. No. 2,621,215, mixtures of chlorinated solvents, in particular tetrachloroethylene and trichloroethane, tend to decompose at an accelerated rate, compared to tetrachloroethylene alone.

In order to overcome problems associated with the instability of chlorinated solvents, a wide variety of stabilizers for them are employed. For example, the above mentioned U.S. Pat. No. 3,787,509 lists a number of different types of compounds that have been found useful in stabilizing trichloroethane against decomposition. Specifically, commercially available trichloroethane obtained under the brand name of Chlorothene VG from the Dow Chemical Co., Midland, Mich., is stabilized by the addition of nitromethane, dioxane and acetonitrile. It is believed that these and similar stabilizers as listed in the U.S. Pat. No. 3,787,509 work as acid scavengers to remove the acid decomposition products of the chlorinated solvents, thus substantially reducing the rate of decomposition.

In the fabrication of integrated circuits and other semiconductor devices, as well as lead frames for them, and the like, freedom of the device surfaces from contamination is very important to assure proper operation of the finished devices. Chlorinated solvents, in particular, trichloroethylene, have achieved a high degree of acceptance as degreasing solvents for the semiconductor devices. In use, the semiconductor devices are immersed in vigorously boiling chlorinated solvents to degrease them. Such semiconductor devices usually include aluminum or other metallization which catalyzes the decomposition of the chlorinated solvents and is also subject to attack by the acid decomposition products of the chlorinated solvents. It thus may be recognized that the degreasing of semiconductor devices represents a difficult environment for use of chlorinated solvents, even if stabilized. Commercially available stabilized trichloroethylene has proved to be satisfactory for this application.

However, a major problem associated with continued use of trichloroethylene for this purpose is that the trichloroethylene molecule contains an unsaturated double bond. Chlorinated solvents containing unsaturated double bonds cannot be discharged into the atmosphere under present Environmental Protection Agency regulations. The ability to continue their use is therefore dependent on the ability to remove them completely from exhaust gases. Various other chlorinated solvents not containing unsaturated double bonds have therefore been considered as replacements for trichloroethylene, since they are not prohibited in exhaust gases. Initial attempts to use trichloroethane in this environment have not been successful. Even the commercially available stabilized Chlorothene VG will withstand decomposition during use described above as a degreasing solvent for semiconductor devices for only about 1 or 2 hours, far too short a time to allow its practical use as such a degreasing solvent.

Thus, while the art of stabilizing chlorinated solvents is a well developed one, there remains a need for a stabilized chlorinated solvent composition which will meet the stringent demands of degreasing semiconductor devices, yet which is acceptable under Environmental Protection Agency regulations.

SUMMARY OF THE INVENTION

Accordingly, it is an object of this invention to provide an improved stabilized chlorinated solvent for use in the manufacture of semiconductor devices.

It is a further object of the invention to provide an improved stabilized chlorinated solvent which will meet the stringent requirements for degreasing semiconductor devices yet which is acceptable from an environmental protection standpoint.

It is another object of the invention to provide an improved stabilizer for 1,1,1-trichloroethane.

It is still another object of the invention to provide a stabilizer for 1,1,1-trichloroethane which has sufficient stabilizing power to allow the resulting composition to be used as a solvent for degreasing semiconductor devices and other components having aluminum or other metallization which will catalyze the decomposition of chlorinated solvents and which is subject to attack by the acid decomposition products of chlorinated solvents.

The attainment of these and related objects is achieved through use of the novel stabilized trichloroethane composition herein disclosed. In accordance with the invention, 1,1,1-trichloroethane may be stabilized through use of a free radical scavenger which will trap trichloromethyl radicals, making them unavailable for formation of acidic species in the trichloroethane. Examples of such free radical scavengers include trichloroethylene, tetrachloroethylene, fluorene, and the like.

While applicants do not intend to be bound by any particular theory of operation, it is believed that the presence of the free radical scavengers in the compositions of this invention tend to trap trichloromethyl radicals as intermediates before the acidic decomposition of these radicals takes place. Consequently, an amount of the free radical scavengers in the compositions of this invention which will decrease the amount of trichlomethyl radicals for formation of the acidic decomposition products of trichloroethane is effective. Generally, the free radical scavengers are provided in an amount of from about 0.1 volume percent to about 5 volume percent of the stabilized composition. In the case of lesser amounts of the free radical scavengers, the compositions will not be stabilized as long as in the case of greater amounts of the free radical scavengers. Generally, the addition of more than about 5 volume percent of the free radical scavengers does not produce additional beneficial effects. However, it has been discovered that the amount of acidic decomposition species from the trichloroethane present in the composition may be monitored, and additional free radical scavenger added to replace that which has been exhausted. Thus, the principal practical effect of adding a lesser amount of the free radical scavenger to the composition is that additional free radical scavenger will need to be added to the composition sooner during its use as a degreasing solvent in order to prevent substantial decomposition of the trichloroethane.

DETAILED DESCRIPTION OF THE INVENTION

Operable free radical scavengers for use in this invention are those which will combine with trichloromethyl radicals in accordance with the following general reaction:

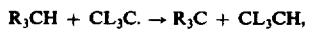

$$R_3CH + CL_3C. \rightarrow R_3C + CL_3CH,$$

as described in, for example, Roberts and Caserio, *Basic Principles of Organic Chemistry* (W. A. Benjamin, Inc., New York, 1964), page 948, the disclosure of which is incorporated by reference herein. Thus, in addition to trichloroethylene, tetrachloroethylene, and fluorene suitable specific examples of such free radical scavengers include toluene, cumene, allylbenzene, bibenzyl, diphenylmethane, triphenylmethane, and the like, all disclosed by Roberts and Caserio as having favorable reaction rates in the above general reaction. However, for best results, those compounds which are liquid at room temperatures, and which have boiling points not substantially disparate to that of the trichloroethane, are preferred. These include trichloroethylene, tetrachloroethylene, toluene, cumene and allylbenzene. Such compounds will be present in appreciable amounts in both the liquid and the vapor phase during reflexing, thus stabilizing both phases.

The following nonlimiting examples describe the invention further and represent preferred modes for practice of the invention.

EXAMPLE 1

Commercially available Chlorothene VG trichloroethane, as received, was refluxed and the acidity of the solvent checked during the refluxing operation in order to provide a standard for comparison of the present invention. A quantity of 400 ml of fresh Chlorothene VG trichloroethane was refluxed and 5 ml samples were withdrawn at the time intervals shown in Table 1.

TABLE I

| SAMPLE | REFLUX TIME(HRS) |
|---|---|
| A1 | 0 (Control) |
| A2 | 2 |
| A3 | 5 |
| A4 | 22 |
| A5 | 48 |
| A6 | 96 |
| A7 | 120 |

One ml of deionized water was added to each 5 ml sample and mixed well. After 15 minutes, the water layer of each sample was tested with pH paper. Samples A1 and A2 were not acidic. Sample A3 was mildly acidic, and the acidity of the water layers increased for the other samples as the reflux time increased. This shows that decomposition of the trichloroethane takes places under the refluxing conditions. Two drops of the water layer from each sample was placed on silicon wafers having a 5,000 A thick aluminum metallization on them, allowed to dry, and the wafers exposed to ambient conditions for twenty four hours. Samples A1 and A2 did not produce corrosion of the aluminum. Slight corrosion of the aluminum was observed with sample A3, and moderate corrosion was observed with sample A4. Samples A5 through A7 showed severe corrosion. The water phase from sample A1 was tested daily for ten days and did not become acidic.

In order better to understand the nature of the acidic species which forms during refluxing, tests to confirm the presence of chloride ion in the water extracts were performed. The formation of silver chloride precipitates after the addition of silver nitrate solution, which do not dissolve when the solution is acidified with diluted nitric acid, confirms the presence of the chloride ion. The water extracts from various lots of fresh Chlorothene VG were tested in this way. In all cases, the tests for the chloride ion were negative. Water extracts taken from Chlorothene VG trichloroethane refluxed for six hours or more gave positive chloride ion tests in all cases. These water extracts also gave an acidic pH. The amount of silver chloride precipitate formed in these tests appeared to be roughly proportional to the length of the reflux time. These tests indicate that the acidic species is probably HCl.

EXAMPLE 2

The procedure of Example 1 was repeated, but 1 ml of trichloroethylene was added to 200 ml of Chlorothene VG trichloroethane prior to refluxing for seventy two hours. A 200 ml sample of the trichloroethane from the same lot was refluxed at the same time as a control. After refluxing for seventy two hours, a water extract of the control had an acid pH, gave a positive chloride ion test and produced corrosion of the aluminum on the test wafer. The water extract from the trichloroethane containing trichloroethylene did not give an acid pH, gave a negative chloride ion test, and did not produce corrosion of the aluminum on the test wafer. The experiment was repeated several times and produced the same results.

EXAMPLE 3

The procedure of Example 2 was repeated, but with use of 1,1,2,2-tetrachloroethylene used in place of the trichloroethylene in Example 2. The same results were obtained, i.e., the water extract from the trichloroethane containing the tetrachloroethylene did not have an acidic pH, gave a negative chloride ion test, and did not produce corrosion of the aluminum on the test wafer.

EXAMPLE 4

Commercially available Chlorothene VG trichloroethane containing 0.5 percent by volume of tetrachloroethylene was employed for degreasing Kovar nickel alloy lead frames in a production scale chemical milling operation over a 10 week period. For comparative purposes, Chlorothene VG trichloroethane containing no tetrachloroethylene was initially used. In each case, the lead frames were placed in vigorously boiling trichloroethane, then suspended in the vapor phase for final rinsing. After about 2 hours of use, the control batch of trichloroethane containing no tetrachloroethylene produced noticeable corrosion of the lead frames. The tetrachloroethylene was then added. The trichloroethane containing tetrachloroethylene did not show corrosion of the lead frames, even after ten weeks of intensive usage.

Substitution of fluorene for the trichloroethylene or tetrachloroethylene in Examples 2 and 3 above in equivalent amounts produces similar advantageous results, except that appreciable amounts of the fluorene do not enter the vapor phase, since the fluorene is present as a solid dissolved in the liquid phase. Substitution of the other free radical scavengers listed previously in equivalent amounts produces similar results.

It should now be apparent that a stabilized trichloroethane solution and process capable of achieving the stated objects of the invention have been provided. Through utilization of a free radical scavenger in accordance with this invention, breakdown of the trichloroethane and consequent formation of acidic biproducts is substantially eliminated. This allows the trichloroethane to be utilized as a degreasing solvent in the fabrication of semiconductor and related devices having aluminum or other metallization subject to attack by acidic biproducts from the decomposition of chlorinated solvents. The result is an environmentally acceptable chlorinated solvent composition highly suitable for use in the semiconductor industry.

While the above examples represent the best modes contemplated for carrying out the invention, it should be apparent to the art skilled that various changes in the composition and process may be made. For example, the free radical scavenging agents may be used in lesser or greater amounts, with the result that they need to be replenished in greater or lesser time intervals. Further, other free radical scavengers may be substituted for the free radical scavengers disclosed. It is intended that such modifications within the spirit and scope of the appended claims be covered thereby.

What is claimed is:

1. A stabilized composition consisting essentially of 1,1,1-trichloroethane and an effective amount of a free radical scavenger selected from the group consisting of trichloroethylene and fluorene which will trap trichloromethyl radicals, making them unavailable for formation of acidic species in said trichloroethane.

2. The composition of claim 1 in which said free radical scavenger is present in an amount of from about 0.1 volume percent to about 5 volume percent.

3. A method for stabilizing 1,1,1-trichloroethane which comprises adding a sufficient amount of a free radical scavenger selected from the group consisting of trichloroethylene and fluorene which will trap trichloromethyl radicals, making them unavailable for formation of acidic species in said trichloroethane.

4. The method of claim 3 wherein said free radical scavenger is present in an amount of from about 0.1 volume percent to about 5 volume percent.

* * * * *